(12) United States Patent
Geppert et al.

(10) Patent No.: US 8,747,839 B2
(45) Date of Patent: Jun. 10, 2014

(54) TRACKING OF BONE MARROW CELLS FOR METASTASIS SCREENING

(75) Inventors: Christian Geppert, Erlangen (DE); Arne Hengerer, Möhrendorf (DE); Sven Meyburg, Erlangen (DE); Sebastian Schmidt, Weisendorf (DE); Susanne Schmolke, Erlangen (DE); Ralph Markus Wirtz, Köln (DE)

(73) Assignees: Siemens Aktiengesellschaft, Munich (DE); Siemens Healthcare Diagnostics Products GmbH, Marburg (DE)

( * ) Notice: Subject to any disclaimer, the term of this patent is extended or adjusted under 35 U.S.C. 154(b) by 576 days.

(21) Appl. No.: 12/974,214

(22) Filed: Dec. 21, 2010

(65) Prior Publication Data
US 2011/0150758 A1    Jun. 23, 2011

(30) Foreign Application Priority Data
Dec. 23, 2009    (DE) .......................... 10 2009 060 317

(51) Int. Cl.
*A01N 63/02*    (2006.01)
*A61K 35/32*    (2006.01)
*A61K 51/02*    (2006.01)
*A61B 5/055*    (2006.01)

(52) U.S. Cl.
USPC .......... 424/93.7; 424/549; 424/1.17; 424/9.3; 424/9.32; 424/9.37; 977/773; 977/930

(58) Field of Classification Search
None
See application file for complete search history.

(56) References Cited

U.S. PATENT DOCUMENTS

2006/0134080 A1*  6/2006  Lyden et al. ................ 424/93.21
2008/0292554 A1   11/2008  Ahrens
2009/0291087 A1* 11/2009  Scott et al. ................. 424/145.1

FOREIGN PATENT DOCUMENTS

WO    WO 0071169 A2    11/2000
WO    WO 2005072780 A2    8/2005

OTHER PUBLICATIONS

Frank et al (Radiology, 2003, vol. 228, pp. 480-487).*
Porada et al (Advanced Drug Delivery Reviews, 2010, vol. 62, pp. 1156-1160).*
Studeny et al (Journal of the National Cancer Institute, 2004, vol. 96, pp. 1593-1603.*
S.A. Anderson et al: "Noninvasive MR imaging of magnetically labeled stem cells to directly identify neovasculature in a glioma maodel" In: Blodd, ISSN 0006-4971, 2005, 105, 420-425; Others; 2005.
German priority document DE 10 2009 060 317.4, filed Dec. 23, 2009, not yet published.

* cited by examiner

*Primary Examiner* — Karen Canella
(74) *Attorney, Agent, or Firm* — Harness, Dickey & Pierce, P.L.C.

(57) ABSTRACT

At least one embodiment of the invention relates to bone marrow precursor cells or bone marrow cells of a patient, the cells labeled with at least one contrast agent suitable for an imaging method, for use in an imaging method for diagnosing a metastasizing cancer, wherein the local accumulation of the labeled precursor cells or bone marrow cells indicates the presence of a metastasizing tumor growth. At least one embodiment also relates to a method for imaging a metastasizing tumor tissue in a patient, wherein a) bone marrow precursor cells or bone marrow cells are extracted from a patient, b) these precursor cells or bone marrow cells are labeled with at least one contrast agent suitable for an imaging method, c) the precursor cells or bone marrow cells thus labeled are retransplanted or reinjected into the patient, and d) the presence of metastasizing tumor cells is depicted with an imaging method. At least one embodiment also relates a method for imaging a metastasizing tumor tissue, wherein a suitable imaging method is used to image bone marrow precursor cells and/or bone marrow cells that are accumulated in a metastasizing tumor tissue and labeled with at least one contrast agent suitable for an imaging method.

22 Claims, No Drawings

TRACKING OF BONE MARROW CELLS FOR METASTASIS SCREENING

PRIORITY STATEMENT

The present application hereby claims priority under 35 U.S.C. §119 on German patent application number DE 10 2009 060 317.4 filed Dec. 23, 2009, the entire contents of which are hereby incorporated herein by reference.

FIELD

At least one embodiment of the invention generally relates to bone marrow precursor cells and/or hematopoietic stem cells from human bone marrow (=bone marrow cells) of a patient, the cells labeled with at least one contrast agent suitable for an imaging method, for use or application in an imaging method for diagnosing a metastasizing cancer. The local accumulation of the labeled bone marrow precursor cells or bone marrow cells in the organism indicates the presence of a metastasizing tumor growth. At least one embodiment of the invention further relates to a method for imaging a metastasizing tumor tissue in a patient using bone marrow precursor cells and/or bone marrow cells that are labeled with at least one contrast agent suitable for an imaging method, and also to a method for imaging a metastasizing tumor tissue involving imaging the bone marrow precursor cells and/or bone marrow cells that are labeled with at least one contrast agent suitable for an imaging method and are accumulated in a metastasizing tumor tissue.

BACKGROUND

Solid tumors require their own vascular supply (neoangiogenesis) for growth, since the supply of nutrients and oxygen by diffusion is insufficient from a certain size. Neoangiogenesis is mediated, inter alia, by osteopontin (OPN), which is secreted at an early stage by aggressive primary tumors and also, as the case may be, by metastasizing tumor cells. OPN causes bone marrow cells which are still undifferentiated and/or more differentiated to migrate from the bone to the metastasizing loci. There the precursor cells differentiate and form a tumor stroma which promotes further tumor growth, and colonization and also neoangiogenesis. Up to 30% of the cellular portion of primary tumors or metastases may originate from these recruited bone marrow cells, which can multiply at the site by further dividing growth before they finally differentiate.

WO 2005/072780 describes reagents and formulations for the ex vivo labeling of cells, with the aim of providing these cells for an imaging technique (MRI, MRS). Preference is given to using fluorocarbon-based imaging reagents for the labeling. There is described a multiplicity of cells which can be labeled and used in a multiplicity of clinical methods.

WO 00/71169 describes the use of MR-sensitive contrast agents for treating living cells in order to be able to provide these cells for MR imaging. The cells thus labeled may be used for diagnostic or therapeutic purposes or for research purposes. The methods and reagents described in this communication are suitable for the labeling of a multiplicity of cells.

S. A. Anderson et al. describe in Blood, vol. 105, no. 1 (2005), pages 420-425, a noninvasive imaging of magnetically labeled stem cells in order to study new vascular formation in a glioma model. The labeling method of this communication is suitable for the monitoring of tumor growth, for the monitoring of the gene therapy for tumors, and also for the monitoring of the therapeutic transplantation of endothelial precursor cells for neovascularization in the case of a brain or heart infarct.

No references to a diagnosis of metastasizing tumors can be found in the prior art.

Metastases are often diagnosed late, since a certain cell number has to be reached before detection is feasible. In most cases, the metastases have already become further advanced and symptomatic at this point, and a curative therapy for metastasizing tumors is therefore no longer possible.

With the methods of the prior art, metastases can only be diagnosed from a certain size. This is achieved, for example, by FDG-PET. Alternatively, for certain tumors, chemotherapy is delivered prophylactically in order to destroy any metastases present. Overall, however, all approaches of the prior art are unsatisfactory for a timely diagnosis or for overcoming the problem of late diagnosis options for metastases.

SUMMARY

There is thus a need for a method with which metastases can be diagnosed at the earliest opportunity.

In at least one embodiment of the invention provides agents and methods with which a metastasizing tumor growth or metastasis formation or aggressive primary tumors can be reliably diagnosed at an early stage. The methods and agents according to at least one embodiment of the invention are intended to be applicable in a simple and gentle manner and are thus suitable for routine checks in connection with cancers. The method according to at least one embodiment of the invention and the agents according to at least one embodiment of the invention are further intended to be suitable for detecting metastasis formation for any tumor type.

The method according to at least one embodiment of the invention is further intended to provide results such that a specific treatment of a particular cancer is possible. Specifically, the method according to at least one embodiment of the invention or the use according to at least one embodiment of the invention is intended to provide results which allow a targeted administration of active substances at the site of the tumor.

It was found that, surprisingly, a group of relatively easy to isolate cells of a patient, i.e., osteoclasts or bone marrow precursor cells and also bone marrow cells, are, after ex vivo labeling with a contrast agent suitable for an imaging method, suitable as molecular "tracking dogs" for detecting metastases at a very early stage.

At least one embodiment of the invention is achieved by bone marrow precursor cells and/or bone marrow cells of a patient, said cells labeled with at least one contrast agent suitable for an imaging method, for use in an imaging method for diagnosing a metastasizing cancer, wherein the local accumulation of the labeled bone marrow precursor cells or bone marrow cells indicate the presence of a metastasizing tumor growth.

At least one embodiment of the invention further relates to a method for imaging a metastasizing tumor tissue in a patient, wherein a) bone marrow precursor cells or bone marrow cells are extracted from a patient, b) these precursor cells or bone marrow cells are labeled with at least one contrast agent suitable for an imaging method, c) the precursor cells or bone marrow cells thus labeled are retransplanted or reinjected into the patient, and d) the presence of metastasizing tumor cells is depicted with an imaging method. Furthermore, at least one embodiment of the invention relates to a method for imaging a metastasizing tumor tissue, characterized in that a suitable imaging method is used to image bone marrow precursor cells or bone marrow cells that are accumulated in a metastasizing tumor tissue and labeled with at least one contrast agent suitable for an imaging method.

With at least one embodiment of this method, data about the location of the tumor tissue are obtained. These data then make it possible to determine, in a further step, the type, scale, and extent of the cancer and to prepare appropriate therapies.

By virtue of at least one embodiment of the invention, a method for treating a metastasizing tumor tissue can be developed, wherein the primary tumor tissue is characterized with regard to therapeutic target molecules by way of molecular biology methods (RNA, DNA, or miRNA analytics) and, after the metastatic tissue has been imaged in a first step by way of the retransplanted or reinjected bone marrow cells, the bone marrow cells of the patient are loaded or labeled by loading them with therapeutically active substances before a second retransplantation.

DETAILED DESCRIPTION OF THE EXAMPLE EMBODIMENTS

Various example embodiments will now be described more fully in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example and will herein be described in detail. It should be understood, however, that there is no intent to limit example embodiments of the present invention to the particular forms disclosed. On the contrary, example embodiments are to cover all modifications, equivalents, and alternatives falling within the scope of the invention.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

When carrying out the use according to at least one embodiment of the invention or the method according to at least one embodiment of the invention, bone marrow cells are extracted from the blood or bone marrow of a cancer patient (e.g., a breast cancer patient) in a manner known per se.

Preferably, the bone marrow cells are LSK cells (Lin−, Sca1+, cKit+). However, use can also be made of more differentiated cells from bone marrow (including various differentiation stages of bone marrow cells and osteoclasts).

Osteoclasts or bone marrow cells can be isolated from blood or bone marrow. Alternatively, mononuclear precursor cells in a cell culture can be differentiated into osteoclasts. To separate the osteoclasts from other cellular constituents of the blood, bone marrow, or the cell culture, known cell sorting methods can be used, for example magnetic sorting after binding to magnetic particles (MACS) or fluorescence-based methods (FACS).

After the osteoclasts have been accumulated, they are labeled with the contrast agent. This can be achieved with a contrast agent comprising a group which mediates binding to the cell, for example, peptides, antibodies, binding sites for surface receptors, such as the transferrin receptor, or which mediates binding to the bone marrow cell markers Sca1 and cKit.

The bone marrow cells are then labeled or loaded ex vivo with at least one contrast agent suitable for an imaging method. Examples of suitable contrast agents are MR contrast agents. Examples for this purpose are perfluorocarbons (PFCs), superparamagnetic iron oxide nanoparticles, SPIO, USPIO, VSPIO, ferrites, Resovist, Supravist, Combidex, paramagnetic ions, such as gadolinium or manganese, or hyperpolarized substances having isotopes, such as 13C or 15N, for example. Alternatively, radioactive substances may be used for detection by nuclear medicine methods, for example gamma emitters, such as technetium, or beta+ emitters, such as 18F, 11C, 13N, or 15O.

Bone marrow cells labeled with perfluorocarbons (PFCs) can, after reinjection, be detected as a hot spot by means of combined 1H/19F MRT. Cells loaded with superparamagnetic iron oxide nanoparticles change the local inhomogeneity of the magnetic field. The result is a locally intensified T2* effect which becomes apparent as a hypointense region in the MRI, and so it is possible to indirectly infer the presence of the labeled cells. Preferably, the bone marrow precursor cells or bone marrow cells are labeled with a contrast agent suitable for an imaging method.

The loading of the bone marrow cells or precursor cells with a contrast agent suitable for an imaging method is carried out according to methods known per se from the prior art, either by a simple incubation with the contrast agent, by biochemical labeling of the cell surface, by electroporation or mediated by a transfection agent, such as polylysine for example.

The cells thus loaded are retransplanted (at the extraction site or in the lymph node), or injected systemically. The cells are retransplanted/reinjected in a manner known per se and at a physiologically compatible concentration.

An example embodiment of the invention is the use of bone marrow cells which are biotinylated at cell surface structures. After the cells thus labeled have been reinjected, they are detected by means of an intravascular injection of streptavidin to which magnetic nanoparticles or fluorochromes are coupled.

There are no indications that there is a change in the integrity and the behavior of the bone marrow cells or precursor cells that are loaded with a contrast agent suitable for an imaging method, and it can therefore be assumed that, like native bone marrow cells or precursor cells, the labeled bone marrow cells or precursor cells are recruited along the OPN gradient to the metastasizing sites. The loaded cells accumulate here and can thus be detected by means of MRI. Double-labeled cells (fluorine and iron oxide) are detected with the aid of both labels. Since the locally accumulated cell number is low and the cells dilute the label as a result of cell division, it is to be expected that no pronounced signal generation by the labeled bone marrow cells or precursor cells occurs. The double label allows the specific search for regions having hot spot genesis (via F19) and signal cancellation (via iron oxide). The difference image increases the sensitivity and specificity. Local accumulations of bone marrow cells thus identified can be examined with a further imaging method (FDG-PET or FDG-MR/PET, DWI MRI, MRS, etc.) for further evaluation. With the aid of the identified localized accumulation, a high-resolution method can then be further applied in the suspected region and the metastasis formation can thus be specifically detected.

Examples of suitable imaging methods for use within the scope of at least one embodiment of the present invention are 1H/19F MRT, FDG-PET, FDG-MR/PET, SPECT, SWI MRT, DWI MRI, and MRS.

According to at least one embodiment of the invention, localized metastasizing spots can be specifically detected in a timely manner. They can thus be specifically treated in a timely manner, for example, by a surgical procedure, Gamma Knife, HIFU, or thermoablation.

The method according to at least one embodiment of the invention or the use according to at least one embodiment of the invention is suitable in general for detecting metastases in many cancers. Examples of these are breast carcinoma, prostate carcinoma, lung carcinoma, colorectal carcinoma, gastric carcinoma, ovarian carcinoma, hepatocellular carcinoma, thyroid carcinoma, renal cell carcinoma, head and neck cancer, bladder carcinoma.

Furthermore, the method according to at least one embodiment of the invention is, after detection of the metastases by the method according to at least one embodiment of invention, suitable in a second step for treating the cells used in a targeted manner and at an exact dose corresponding to the accumulation levels determined in the first step of the method, by loading them with active substances. For this purpose, it is worth considering, inter alia, loading with osteopontin-specific aptamers (RNA/DNA or peptide-based) owing to the osteopontin-mediated recruitment of bone marrow cells.

Patients whose primary tumors indicate an increased expression of osteopontin at the RNA or protein level and patients whose osteopontin protein levels in the blood or serum are increased are especially suitable for the method according to the invention. Patients who are especially predestined for the method according to at least one embodiment of the invention can thus be selected or stratified by upstream in vitro diagnostic methods.

The method is also suitable for tracking primary tumors in patients having an unknown original tumor (=CUP, cancer of unknown primary), who can subsequently be treated more adequately with a therapy specific for the tumor type.

The ability of metastatic tissues to recruit injected bone marrow cells likewise correlates with the angiogenic activity of the tumor and tumor stroma. Accordingly, the method according to at least one embodiment of the invention is also suitable for identifying tumors which benefit from an antiangiogenic therapy. Accordingly, the kinetics and the degree of the accumulation of bone marrow cells is indicative of the reaction to substances, such as those listed as follows: BAY 43-9005 (target molecule: VEGFR-2, VEGFR-3, c-KIT, PDGFR-B, RET, and Raf kinase), BAY 57-9352 (target molecule: VEGFR-2), sunitinib (trade name: Sutent®; target molecule: VEGFR-1, VEGFR-2, and PDGFR), AG13925 (target molecule: VEGFR-1 and VEGFR-2), AG013736 (target molecule: VEGFR-1 and VEGFR-2), AZD2171 (target molecule: VEGFR-1 and VEGFR-2), ZD6474 (target molecule: VEGFR-1, VEGFR-2, and VEGFR-3), PTK-787/ZK-222584 (target molecule: VEGFR-1 and VEGFR-2), CEP-7055 (target molecule: VEGFR-1, VEGFR-2, and VEGFR-3), CP-547 (target molecule: VEGFR-1 and VEGFR-2), CP-632 (target molecule: VEGFR-1 and VEGFR-2), GW786024 (target molecule: VEGFR-1, VEGFR-2, and VEGFR-3), AMG706 (target molecule: VEGFR-1, VEGFR-2, and VEGFR-3), imatinib mesylate (trade name: Glivec®/Gleevec®; target molecule: bcr-abl and c-KIT), BMS-214662 (target molecule: Ras farnesyltransferase), CCI-779 (target molecule: mTOR), RAD0001 (trade name: Everolismus®; target molecule: mTOR), CI-1040 (target molecule: MEK), SU6668 (target molecule: VEGFR-2, PDGFR-B, and FGFR-1), AZD6126, CP547632 (target molecules: VEGFRs), CP868596 GW786034 (target molecules: PDGFRs), ABT-869 (target molecules: VEGFRs and PDGFRs), AEE788 (target molecules: VEGFRs and PDGFRs), AZD0530 (target molecules: src and abl), and CEP7055.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of diagnosing a tumor, the method comprising:
   administering to a patient osteoclasts labeled with at least one contrast agent suitable for a non-invasive imaging method; and
   performing the non-invasive imaging method, wherein a local accumulation of the labeled osteoclasts indicates presence of the tumor.

2. The method as claimed in claim 1, wherein the contrast agent suitable for the non-invasive imaging method is selected from the group consisting of perfluorocarbons (PFCs), superparamagnetic iron oxide nanoparticles, biotin-labeled streptavidin, paramagnetic ions, and hyperpolarized substances having isotopes.

3. The method as claimed in claim 1, wherein the non-invasive imaging method is selected from the group consisting of 1H/19F MRT, FDG-PET, FDG-MR/PET, DWI MRT, and MRS.

4. The method as claimed in claim 1, wherein the tumor is breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

5. The method as claimed in claim 2, wherein the non-invasive imaging method is selected from the group consisting of 1H/19F MRT, FDG-PET, FDG-MR/PET, DWI MRT, and MRS.

6. The method as claimed in claim 2, wherein the tumor is breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

7. The method as claimed in claim 3, wherein the tumor is breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

8. The method as claimed in claim 5, wherein the tumor is breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

9. A method for imaging a tumor tissue in a patient, comprising:
    extracting an osteoclast from a patient;
    labeling the osteoclast with at least one contrast agent suitable for a non-invasive imaging method;
    retransplanting or reinjecting the labeled osteoclast into the patient; and
    depicting presence of the tumor tissue with the non-invasive imaging method.

10. The method as claimed in claim 9, wherein the contrast agent suitable for the non-invasive imaging method is selected from the group consisting of perfluorocarbons (PFCs), superparamagnetic iron oxide nanoparticles, biotin-labeled streptavidin, paramagnetic ions, and hyperpolarized substances having isotopes.

11. The method as claimed in claim 9, wherein the non-invasive imaging method is selected from the group consisting of 1H/19F MRT, FDG-PET, FDG-MR/PET, DWI MRT, and MRS.

12. The method as claimed in claim 9, wherein the tumor tissue is a breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

13. The method as claimed in claim 10, wherein the non-invasive imaging method is selected from the group consisting of 1H/19F MRT, FDG-PET, FDG-MR/PET, DWI MRT, and MRS.

14. The method as claimed in claim 10, wherein the tumor tissue is a breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

15. The method as claimed in claim 11, wherein the tumor tissue is a breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

16. A method for imaging tumor tissue, comprising:
    administering osteoclasts labeled with at least one contrast agent suitable for a non-invasive imaging method to a patient from which the osteoclasts were extracted; and
    using the suitable non-invasive imaging method to image the labeled osteoclasts that are accumulated in a tumor tissue.

17. The method as claimed in claim 16, wherein the contrast agent suitable for the non-invasive imaging method is selected from the group consisting of perfluorocarbons (PFCs), superparamagnetic iron oxide nanoparticles, biotin-labeled streptavidin, paramagnetic ions, and hyperpolarized substances having isotopes.

18. The method as claimed in claim 16, wherein the non-invasive imaging method is selected from the group consisting of 1H/19F MRT, FDG-PET, FDG-MR/PET, DWI MRT, and MRS.

19. The method as claimed in claim 16, wherein the tumor tissue originates from a breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

20. The method as claimed in claim 17, wherein the non-invasive imaging method is selected from the group consisting of 1H/19F MRT, FDG-PET, FDG-MR/PET, DWI MRT, and MRS.

21. The method as claimed in claim 17, wherein the tumor tissue originates from a breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

22. The method as claimed in claim 18, wherein the tumor tissue originates from a breast carcinoma, prostate carcinoma, lung carcinoma, hepatocellular carcinoma, colorectal carcinoma, gastric carcinoma, ovarian carcinoma, thyroid carcinoma, renal cell carcinoma, head and neck cancer, or bladder carcinoma.

* * * * *